United States Patent [19]
Sakata et al.

[11] Patent Number: 4,665,038
[45] Date of Patent: May 12, 1987

[54] COMPOSITION, METHOD AND TEST STRIP FOR EXAMINING UROBILINOGEN

[75] Inventors: Yoshitsugu Sakata, Otsu; Tadashi Hamanaka, Kobe; Kenzi Iwata, Higashiosaka; Misato Nakaue, Sakai, all of Japan

[73] Assignee: Wako Pure Chemical Industries, Ltd., Osaka, Japan

[21] Appl. No.: 660,201

[22] Filed: Oct. 12, 1984

[30] Foreign Application Priority Data

Oct. 15, 1983 [JP] Japan ................................. 58-193127

[51] Int. Cl.$^4$ ...................... G01N 33/50; G01N 33/48
[52] U.S. Cl. ........................................ 436/97; 422/56; 436/903
[58] Field of Search ................... 436/97, 903; 422/56, 422/57; 534/563, 559

[56] References Cited

U.S. PATENT DOCUMENTS 3,692,836  9/1972  Troxler et al. ...................... 534/563
3,850,576  11/1974  Rittersdorf et al. ................. 436/97
3,989,462  11/1974  Hirsch ................................. 436/97

FOREIGN PATENT DOCUMENTS 2311303  12/1976  France .................................. 436/97
114954  9/1980  Japan .................................... 436/97

OTHER PUBLICATIONS

Beilstein Syst. No. 2200, Vgl S 426, Dis 428, Jan. 1910.
Chemical Abstracts, vol. 96, 1982, 172125t.
Chemical Abstracts 78, 156279u, 1973.
Ibid., 80, 14277ob, 1974.
Ibid., 86: 13522x, 1977.
Ibid., 94: 43712s, 1981.

Primary Examiner—S. Leon Bashore
Assistant Examiner—K. M. Hastings
Attorney, Agent, or Firm—Armstrong, Nikaido, Marmelstein & Kubovcik

[57] ABSTRACT

A composition comprising a 9-fluorenone-2-diazonium salt, an acid or acidic salt which is solid at normal temperatures, and if necessary an anionic surface active agent can produce a vivid red color instantly by reacting with urobilinogen without interfered with bilirubin.

10 Claims, No Drawings

COMPOSITION, METHOD AND TEST STRIP FOR EXAMINING UROBILINOGEN

BACKGROUND OF THE INVENTION

This invention relates to a composition for examining urobilinogen in the urine.

Urobilinogen is produced from the bile appeared in the intestines by reductive action of bacteria. A part of the urobilinogen is absorbed by the portal vein and passed to the liver, while almost all the urobilinogen is ingested by liver cells, excreted in the bile as it is, and led to the intestines. But a part of it passes through the liver and enters into the systemic circulation, and further excreted in the urine.

The amount of urobilinogen in the urine increases in the case of liver function disorder, hemolytic diseases and ileus. Therefore, the examination of urobilinogen in the urine is one of important clinical examinations in the diagnosis of these diseases.

As methods for measuring urobilinogen; there has widely been used a method of using a test paper wherein there is used the condensation reaction between p-dimethylaminobenzaldehyde and urobilinogen to produce a reddish violet color. But this method had defects in that (1) the color-producing reaction is slow and it requires 1 minute or more for the determination, (2) it lacks in specificity and false positive reactions take place by the presence of porphobillinogen, indole, skatole, etc., and (3) a large amount of urea present in the urine reacts with p-dimethylaminobenzaldehyde to produce a yellow color which interfers the determination.

In order to remove such defects, there are reported various color-producing methods using diazonium salts which are faster in the reaction rate for urobilinogen and higher in specificity than p-dimethylaminobenzaldehyde. Generally speaking, diazonium salts also react with bilirubin, but it is possible to measure urobilinogen without influenced by bilirubin by applying the difference in electron affinity of the diazonium salts. For example, it is proposed to use a benzenediazonium salt wherein at least one substituent at the ortho or para position of a phenyl group is a multiatomic electron donating group having at least one mesomeric electron pair and the total of Hammet's $\sigma$ values of all the substituents is not exceeding +0.4 (Ger. Offen. 2,130,559, Chem. Abstr. 78, 1973, 156279u). It is also proposed to use a diazonium salt selected from phenyl-, pyrrole- and pyrazolediazonium salts that are eventually fused or directly substituted with iso- or heterocyclic aromatic compounds in a mesomeric-like and sterically unhindered position, as well as pyridine- and pyrazoldiazonium salts that in a mesomeric position at least one polyatomic electron donar group with at least one measomeric active pair of electrons, the total of Hammet's $\sigma$ values of all substituents and hetero-atoms not exceeding +0.6 (Ger. Offen. 2,229,611, Chem. Abstr. 80, 1974, 142770b). It is further proposed to use 4-fluoro-3-nitrobenzenediazonium salts (U.S. Pat. No. 3,989,462) and anthraquinone series diazonium salts (Japanese Patent Appln. Kokai (Laid-Open) No. 114954/80, Chem. Abstr. 94:43712S, 1981). But these diazonium salts are low in sensitivity for color production with urobilinogen (molecular extinction coefficient: $\epsilon = 8,000-17,000$) and since the color produced is brown to orange in many cases, it is difficult to determine when the urine is colored darkly.

SUMMARY OF THE INVENTION

It is an object of this invention to provide a composition for examining urobilinogen, said composition being able to react with urobilinogen specifically and rapidly, and excellent is sensitivity for color production, and giving a vivid color tone which is by far different from that of the urine.

This invention provides a composition for examining urobilinogen comprising a diazonium salt represented by the formula:

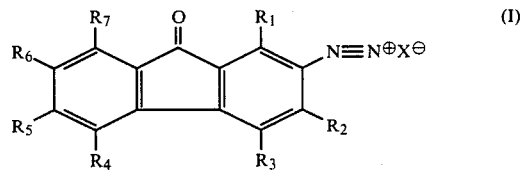

wherein $R_1$ through $R_7$ are independently a hydrogen atom, a halogen atom, a lower alkyl group or a lower alkoxy group; and X is a stabilizing anion, and an acid or acidic salt which is solid at normal temperatures.

DESCRIPTION OF THE PREFERRED EMBODIMENTS

Many diazonium salts produce a brown color when reacted with urobilinogen, said brown color being similar to that of deeply colored urine and making the judgement difficult. But the diazonium salt used in this invention is characterized by reacting with urobilinogen almost instantly and producing a very specific red dye. For example, 9-fluorenone-2-diazonium salt which is a compound having hydrogen atoms at $R_1$ through $R_7$ in the formula (I) is used for examining urobilinogen, $\lambda_{max}$ (wavelength of maximum absorption) of the diazocoupling compound is 500 nm and the molecular extinction coefficient ($\epsilon$) is $2.06 \times 10^4$. Further, the diazonium salt used in this invention has a great advantage in that the color production is not interfered with bilirubin. Therefore, it becomes possible to make a remarkably accurate judgement, which results in greatly contributing to this art.

The composition for examining urobilinogen of this invention includes as a color-producing reagent a diazonium salt represented by the formula:

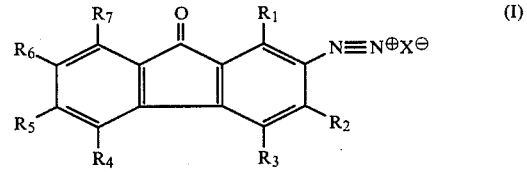

wherein $R_1$ through $R_7$ are independently a hydrogen atom, a halogen atom, a lower alkyl group or a lower alkoxy group; and X is a stabilizing anion.

The lower alkyl group is the definition of $R_1$ through $R_7$ includes an alkyl group preferably having 1 to 4 carbon atoms. Among them, methyl, ethyl and propyl groups are preferable. The lower alkoxy group in the definition of $R_1$ through $R_7$ includes an alkoxy group preferably having 1 to 4 carbon atoms. Among them, methoxy and ethoxy groups are preferable. As the halogen atom, any one of Cl, Br, F and I can be used. The stabilizing anion $X^\ominus$ necessary for use as stable diazonium salt includes anions such as chloride, sulfate, tetrafluoroborate, tetrachlorozincate, trifluoromethylsulfonate, hexafluoroantimonate, arylsulfonate, etc. Among them, tetrafluoroborate is more preferable due to better stability.

Examples of the diazonium salt of the formula (I) are 9-fluorenone-2-diazonium tetrafluoroborate, 3-chloro-9-fluorenone-2-diazonium tetrafluoroborate, 7-methoxy-9-fluorenone-2-diazonium sulfate, 3-methyl-9-fluorenone-2-diazonium tetrafluoroborate, 3,6-dichloro-9-fluorenone-2-diazonium tetrafluoroborate, 1,4-dimethoxy-9-fluorenone-2-diazonium chloride, 3-bromo-9-fluorenone-2-diazonium chloride, 1,3-dibromo-9-fluorenone-2-diazonium sulfate, 3-ethoxy-9-fluorenone-2-diazonium tetrafluoroborate, and 7-chloro-9-fluorenone-2-diazonium tetrafluoroborate.

The diazonium salt of the formula (I) can be prepared by reacting a compound of the formula:

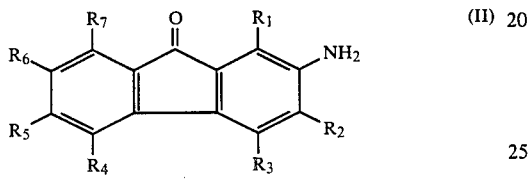

(II)

wherein $R_1$ through $R_7$ are as defined above, with $NaNO_2$ in the presence of hydrochloric acid or sulfuric acid at lower temperatures (e.g. $-5°$ to $+10°$ C.), and if necessary further reacting with M·X wherein M is an alkali metal and X is as defined above.

The composition of this invention further includes an acid or acidic salt which is solid at normal temperatures. The acid or acidic salt is used for giving a strong color production in the reaction between the diazonium salt of the formula (I) and urobilinogen under acidic pH conditions and for improving the stability of the color produced. Examples of the acid or acidic salt which is solid at normal temperatures are inorganic or organic acids and acidic salts such as sulfosalicylic acid, oxalic acid, maleic acid, tartaric acid, citric acid, succinic acid, sulfamic acid, p-toluenesulfonic acid, potassium hydrogensulfate, metaphosphoric acid, p-aminobenzoic acid, pyromellitic dianhydride, etc. These acids or acidic salts can be used alone or as a mixture thereof.

In order to accelerate the reaction with urobilinogen and to improve the sensitivity for color production, it is preferable to add an anionic surface active agent to the composition of this invention. Examples of the anionic surface active agent are sodium dodecylbenzenesulfonate, sodium lacrylsulfate, etc.

The composition of this invention can practically be used in the form of conventionally used test sheet obtained by impregnating a support having water absorption properties with a solution of the composition and drying it.

As the support having water absorption properties, there can be used filter paper, polyester fleece, polyamide fleece, glass fibers, and the like.

In the production of the test sheet, the composition of this invention is mixed with a solvent such as water, an organic solvent which is miscible with water but not reacts with the diazonium salt of the formula (I), e.g. methanol, ethanol, acetone, N,N-dimethylformamide, etc., or a mixture thereof.

The solution of the composition of this invention for impregnation comprises preferably 0.034 to 3.4 mmole, more preferably 0.068 to 0.68 mmole of the diazonium salt of the formula (I) per 100 ml of the whole solution, preferably 1 to 30 g, more preferably 5 to 20 g of the acid or acidic salt per 100 ml of the whole solution, and preferably 0.01 to 2 g, more preferably 0.1 to 1 g of the anionic surface active agent per 100 ml of the whole solution.

After impregnation with the above-mentioned solution, the support is dried in a conventional manner to give a test sheet. The test sheet may be bonded to a supporting member such as a plastic sheet, a thick paper board using an adhesive to give a test material for examining urobilinogen.

The amount of urobilinogen in a urine sample can be determined by immersing a test sheet of this invention in the urine sample, and observing the degree of coloring of the test sheet produced by the reaction with urobilinogen.

The composition for examining urobilinogen of this invention can usually be used in a hand method using a test sheet as mentioned above, wherein the judgement for the test results is conducted by comparing the color tone produced by the reaction with urobilinogen in a sample with that of standard previously prepared after a predetermined time. It is also possible to contact a solution of the composition for examining urobilinogen of this invention with a sample solution and to determine quantitatively the amount of urobilinogen spectrometrically by using a suitable wavelength. Application of the composition of this invention to an auto analyzer is also possible.

This invention is illustrated by way of the following Examples.

REFERENCE EXAMPLE (1) Production of 9-fluorenone-2-diazonium tetrafluoroborate 2-Amino-9-fluorenone in an amount of 12.2 g was suspended in 50 ml of 5N HCl and stirred at 0°–5° C. for 1 hour. To the above-mentioned suspension, 10 ml of ice-cooled aqueous solution of 40 w/v% sodium nitrite was added dropwise so as not to raise the temperature to 10° C. or higher, followed by stirring for 30 minutes.

Cold water was added to the reaction solution to completely dissolve a precipitate of a diazonium salt and insolubles were removed by filtration. To the filtrate, 30 ml of aqueous solution of 32.5 w/v% sodium tetrafluoroborate was added dropwise while stirring at 0°–5° C. After completion of the dropwise addition, the stirring was continued for 30 minutes. Crystals produced were removed by filtration, washed with 30 ml of cold water thrice, washed with 25 ml of ethyl ether twice and dried under reduced pressure to give 12.9 g of yellow crystals of 9-fluorenone-2-diazonium tetrafluoroborate (yield 70%).

(2) Identification of 9-fluorenone-2-diazonium tetrafluoroborate (A) Thin Layer Chromatography (TLC)
  Adsorbent: silica gel
  Developer: ethanol:benzene (3:7 by volume)
  Color-producing reagent: iodine
  TLC spot: One spot was shown at $R_f=0.79$.

(B) UV Absorption Spectrum
  Reference: N,N-dimethylformamide (DMF)
  Solvent: DMF
  $\lambda_{max}$: 300 nm
  Molecular extinction coefficient: about $3.1 \times 10^4$ (C) Infrared Absorption Spectrum Major: about 3450 cm$^{-1}$, 1710 cm$^{-1}$, 1600 cm$^{-1}$, absorptions: 1080 cm$^{-1}$ and 750 cm$^{-1}$.

EXAMPLE 1

(1) Test sheets were produced by impregnating filter paper (for chromatography) with the following impregnating solution, and air-flow drying at 40° C., followed by drying under reduced pressure for 1 hour.

(i) Impregnating solution

| | |
|---|---|
| 9-fluorenone-2-diazonium tetrafluoroborate | 40 mg |
| sulfosalicylic acid | 16 g |
| sodium dodecylbenzenesulfonate | 0.4 g |
| methanol | 30 ml |
| water | sufficient to make 100 ml |

(2) Preparation of urobilinogen standard solutions

Urobilinogen synthesized by catalytic reduction of bilirubin with hydrogen was added to normal urine to give a standard solution containing urobilinogen in concentration of 12 mg/dl. The standard solution was further diluted with urine to give diluted standard solutions containing urobilinogen in concentrations of 8 mg/dl and 4 mg/dl.

(3) Examination

The test sheets thus produced were reacted with urine and the urobilinogen standard solutions to produce colors as shown in Table 1 in 5 to 10 seconds.

TABLE 1

| Sample No. | Urobilinogen concentration (mg/dl) | Degree of coloring |
|---|---|---|
| 1 | about 0.5 (normal urine) | Pinkish white |
| 2 | 4 | Pink |
| 3 | 8 | Reddish pink |
| 4 | 12 | Dark reddish pink |

EXAMPLE 2

(1) Test sheets were produced by impregnating filter paper (for chromatography) with the following impregnating solution and air-flow drying at 30° C., followed by drying under reduced pressure for 1 hour.

(i) Impregnating solution

| | |
|---|---|
| 9-fluorenone-2-diazonium tetrafluoroborate | 40 mg |
| metaphosphoric acid | 10 g |
| sodium laurylsulfate | 0.4 g |
| methanol | 20 ml |
| water | sufficient to make 100 ml |

(2) Preparation of urobilinogen standard solutions

The procedures of Example 1 were repeated.

(3) Examination

The test sheets thus produced were reacted with urine and the urobilinogen standard solutions to produce colors as shown in Table 2 in 5 to 10 seconds.

TABLE 2

| Sample No. | Urobilinogen concentration (mg/dl) | Degree of coloring |
|---|---|---|
| 1 | about 0.5 (normal urine) | Pinkish white |
| 2 | 4 | Pink |
| 3 | 8 | Reddish pink |
| 4 | 12 | Dark reddish pink |

EXAMPLE 3

(1) Test sheets were produced by impregnating filter paper (for chromatography) with the following impregnating solution and air-flow drying at 40° C., followed by drying under reduced pressure for 1 hour.

(i) Impregnating solution

| | |
|---|---|
| 3-chloro-9-fluorenone-2-diazonium tetrafluoroborate | 40 mg |
| sulfosalicylic acid | 5 g |
| sodium dodecylbenzenesulfonate | 0.4 g |
| methanol | 30 ml |
| water | sufficient to make 100 ml |

(2) Preparation of urobilinogen standard solutions

The procedures of Example 1 were repeated.

(3) Examination

The test sheets thus produced were reacted with urine and the urobilinogen standard solutions to produce colors as shown in Table 3 in 5 to 10 seconds.

TABLE 3

| Sample No. | Urobilinogen concentration (mg/dl) | Degree of coloring |
|---|---|---|
| 1 | about 0.5 (normal urine) | Pinkish white |
| 2 | 4 | Pink |
| 3 | 8 | Reddish Pink |
| 4 | 12 | Red |

EXAMPLE 4

(1) Test sheets were produced by impregnating filter paper (for chromatography) with the following impregnating solution and air-flow drying at 30° C., followed by drying under reduced pressure for 1 hour.

(i) Impregnating solution

| | |
|---|---|
| 7-methoxy-9-fluorenone-2-diazonium sulfate | 40 mg |
| oxalic acid | 8 g |
| sodium laurylsulfate | 0.4 g |
| methanol | 20 ml |
| water | sufficient to make 100 ml |

(2) Preparation of urobilinogen standard solutions

The procedures of Example 1 were repeated.

(3) Examination

The test sheets thus produced were reacted with urine and the urobilinogen standard solutions to produce colors as shown in Table 4 in 5 to 10 seconds.

TABLE 4

| Sample No. | Urobilinogen concentration (mg/dl) | Degree of coloring |
|---|---|---|
| 1 | about 0.5 (normal urine) | Pinkish white |
| 2 | 4 | Pink |
| 3 | 8 | Reddish pink |
| 4 | 12 | Dark reddish pink |

EXAMPLE 5

(1) Test sheets were produced in the same manner as described in Example 1 except for using the following impregnating solution.

(i) Impregnating solution

| 3-methyl-9-fluorenone-2-diazonium tetrafluoroborate | 40 mg |
|---|---|
| sulfosalicylic acid | 10 g |
| sodium dodecylbenzenesulfonate | 0.4 g |
| methanol | 30 ml |
| water | sufficient to make 100 ml |

(2) Preparation of urobilinogen standard solutions
The procedures of Example 1 were repeated.

(3) Examination
The test sheets thus produced were reacted with urine and the urobilinogen standard solutions to produce colors as shown in Table 5 in 5 to 10 seconds.

TABLE 5

| Sample No. | Urobilinogen concentration (mg/dl) | Degree of coloring |
|---|---|---|
| 1 | about 0.5 (normal urine) | Pinkish white |
| 2 | 4 | Pink |
| 3 | 8 | Reddish pink |
| 4 | 12 | Red |

EXAMPLE 6

(1) Test sheets were produced in the same manner as described in Example 2 except for using the following impregnating solution.

(i) Impregnation solution

| 3,6-dichloro-9-fluorenone-2-diazonium tetrafluoroborate | 40 mg |
|---|---|
| metaphosphoric acid | 10 g |
| sodium dodecylbenzenesulfonate | 0.4 g |
| methanol | 30 ml |
| water | sufficient to make 100 ml |

(2) Preparation of urobilinogen standard solutions
The procedures of Example 2 were repeated.

(3) Examination
The test sheets thus produced were reacted with urine and the urobilinogen standard solutions to produce colors as shown in Table 6 in 5 to 10 seconds.

TABLE 6

| Sample No. | Urobilinogen concentration (mg/dl) | Degree of coloring |
|---|---|---|
| 1 | about 0.5 (normal urine) | Pink |
| 2 | 4 | Reddish pink |
| 3 | 8 | Red |
| 4 | 12 | Dark red |

EXAMPLE 17

(1) Test sheets were produced by impregnating filter paper (for chromatography) with the following impregnating solution and air-flow drying at 30° C., followed by drying under reduced pressure for 1 hour.

(i) Impregnating solution

| 9-fluorenone-2-diazonium tetrafluoroborate | 100 mg |
|---|---|
| metaphosphoric acid | 10 g |
| sulfosalicylic acid | 1.0 g |
| sodium laurylsulfate | 0.4 g |
| DMF | 10 ml |
| aceton | 20 ml |
| water | sufficient to make 100 ml |

(2) Preparation of urobilinogen standard solutions
The procedures of Example 1 were repeated.

(3) Examination
The test sheets thus produced were reacted with urine and the urobilinogen standard solutions to produce colors as shown in Table 7 in 5 to 10 seconds.

TABLE 7

| Sample No. | Urobilinogen concentration (mg/dl) | Degree of coloring |
|---|---|---|
| 1 | about 0.5 (normal urine) | Pinkish white |
| 2 | 4 | Pink |
| 3 | 8 | Reddish pink |
| 4 | 12 | Dark reddish pink |

What is claimed is:

1. A composition for examining urobilinogen comprising a diazonium salt represented by the formula:

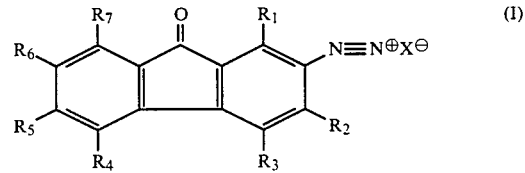

wherein $R_1$ through $R_7$ are independently a hydrogen atom, a halogen atom, a lower alkyl group or a lower alkoxy group; and X is a stabilizing anion, and further comprising an acid or acidic salt which is solid at normal temperatures and which will produce acidic pH conditions in aqueous solution.

2. A composition according to claim 1, wherein the diazonium salt represented by the formula (I) is 9-fluorenone-2-diazonium tetrafluoroborate, 3-chloro-9-fluorenone-2-diazonium tetrafluoroborate, 7-methoxy-9-fluorenone-2-diazonium sulfate, 3-methyl-9-fluorenone-2-diazonium tetrafluoroborate, or 3,6-dichloro-9-fluorenone-2-diazonium tetrafluoroborate.

3. A composition according to claim 1, wherein the acid or acid salt is sulfosalicylic acid, oxalic acid, maleic acid, tartaric acid, citric acid, succinic acid, sulfamic acid, p-toluenesulfonic acid, p-aminobenzoic acid, pyromellitic dianhydride, potassium hydrogensulfate, or metaphosphoric acid.

4. A composition according to claim 1, which further comprises an anionic surface active agent.

5. A composition according to claim 4, wherein the anionic surface active agent is sodium dodecylbenzenesulfonate or sodium laurylsulfate.

6. A test sheet for examining urobilinogen comprising a support having water absorption properties and a composition carried on the support comprising a diazonium salt represented by the formula:

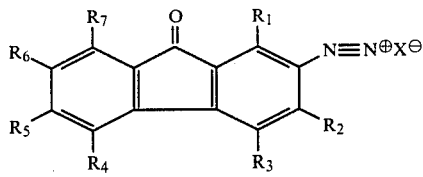

(I)

wherein $R_1$ through $R_7$ are independently a hydrogen atom, a halogen atom, a lower alkyl group or a lower alkoxy group; and X is a stabilizing anion, and further comprising an acid or acidic salt which is solid at normal temperatures.

7. A test sheet according to claim 6, wherein the composition further comprises an anionic surface active agent.

8. A test sheet according to claim 7, which is produced by impregnating a support having water absorption properties with a solution of composition comprising 0.034 to 3.4 mmole of the diazonium salt of the formula (I), 1 to 30 g of the acid or acidic salt which is solid at normal temperatures, and 0.01 to 2 g of the anionic surface active agent per 100 ml of the solution, and drying the support.

9. A method of testing a sample solution for urobilinogen comprising;

(a) obtaining a sample solution to be tested;
(b) contacting the sample solution with a urobilinogen examining composition comprising, a diazonium salt represented by the formula:

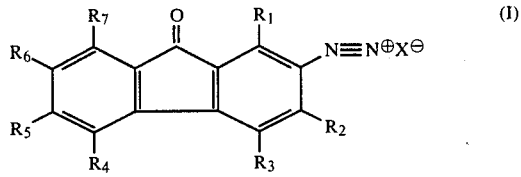

(I)

wherein $R_1$ through $R_7$ are independently a hydrogen atom, a halogen atom, a lower alkyl group or a lower alkoxy group; and X is a stabilizing anion, and further comprising an acid or acidic salt which is solid at normal temperatures, and;

(c) quantitatively determining the amount of urobilinogen based upon analysis of any color produced.

10. The method for testing a sample for urobilinogen as in claim 9 wherein the composition for examining urobilinogen is carried on a support having water absorption properties, to form a test sheet, and the test sheet is contacted with the sample solution to be tested.

* * * * *